US012222352B2

(12) United States Patent
Pimentel et al.

(10) Patent No.: US 12,222,352 B2
(45) Date of Patent: Feb. 11, 2025

(54) DIAGNOSIS OF SCLERODERMA

(71) Applicant: Cedars-Sinai Medical Center, Los Angeles, CA (US)

(72) Inventors: Mark Pimentel, Los Angeles, CA (US); Daniel Furst, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 661 days.

(21) Appl. No.: 16/476,480

(22) PCT Filed: Jan. 29, 2018

(86) PCT No.: PCT/US2018/015723
§ 371 (c)(1),
(2) Date: Jul. 8, 2019

(87) PCT Pub. No.: WO2018/140869
PCT Pub. Date: Aug. 2, 2018

(65) Prior Publication Data
US 2021/0405046 A1    Dec. 30, 2021

Related U.S. Application Data

(60) Provisional application No. 62/451,923, filed on Jan. 30, 2017.

(51) Int. Cl.
*G01N 33/53* (2006.01)
*G01N 33/564* (2006.01)

(52) U.S. Cl.
CPC ....... *G01N 33/564* (2013.01); *G01N 2800/24* (2013.01)

(58) Field of Classification Search
CPC ............. G01N 33/564; G01N 2800/24; G01N 2800/104; G01N 33/53; G01N 33/543
See application file for complete search history.

(56) References Cited

U.S. PATENT DOCUMENTS

| | | | |
|---|---|---|---|
| 5,691,151 A | 11/1997 | Braun et al. | |
| 6,805,852 B2 | 10/2004 | Lin et al. | |
| 6,861,053 B1 | 3/2005 | Lin et al. | |
| 7,048,906 B2 | 5/2006 | Lin et al. | |
| 7,056,686 B2 | 6/2006 | Lin et al. | |
| 7,081,239 B2 | 7/2006 | Lin | |
| 7,244,412 B2 | 7/2007 | Lin | |
| 7,452,857 B2 | 11/2008 | Lin et al. | |
| 7,585,838 B2 | 9/2009 | Lin et al. | |
| 7,605,240 B2 | 10/2009 | Lin et al. | |
| 7,608,245 B2 | 10/2009 | Lin | |
| 7,615,207 B2 | 11/2009 | Lin | |
| 7,718,608 B2 | 5/2010 | Lin et al. | |
| 7,736,622 B2 | 6/2010 | Lin et al. | |
| 7,935,799 B2 | 5/2011 | Lin et al. | |
| 8,110,177 B2 | 2/2012 | Lin et al. | |
| 8,197,805 B2 | 6/2012 | Lin et al. | |
| 8,388,935 B2 | 3/2013 | Lin et al. | |
| 8,562,952 B2 | 10/2013 | Lin et al. | |
| 9,110,081 B2 | 8/2015 | Pimentel et al. | |
| 9,358,276 B2 | 6/2016 | Lin et al. | |
| 9,702,884 B2 | 7/2017 | Pimentel et al. | |
| 9,851,361 B2 | 12/2017 | Pimentel | |
| 9,869,676 B2 | 1/2018 | Pimentel et al. | |
| 9,952,223 B2 | 4/2018 | Pimentel et al. | |
| 10,132,814 B2 | 11/2018 | Pimentel et al. | |
| 10,151,752 B2 | 12/2018 | Pimentel et al. | |
| 10,352,944 B2 | 7/2019 | Pimentel et al. | |
| 10,466,254 B2 | 11/2019 | Pimentel et al. | |
| 10,527,621 B2 | 1/2020 | Pimentel et al. | |
| 10,690,679 B2 | 6/2020 | Pimentel et al. | |
| 2003/0157159 A1 | 8/2003 | Franklin et al. | |
| 2003/0170726 A1 | 9/2003 | Fradelizi et al. | |
| 2004/0018528 A1 | 1/2004 | Morimoto et al. | |
| 2004/0106590 A1 | 6/2004 | Eisenstein | |
| 2006/0127359 A1 | 6/2006 | Borrelli | |
| 2006/0193871 A1 | 8/2006 | Lin | |
| 2007/0212691 A1 | 9/2007 | Yamasaki et al. | |
| 2009/0028940 A1 | 1/2009 | Jahagirdar et al. | |
| 2009/0298060 A1 | 12/2009 | Lal et al. | |
| 2010/0292300 A1* | 11/2010 | Van De Water | A61P 17/02 435/375 |
| 2011/0183337 A1 | 7/2011 | Von Stein et al. | |

(Continued)

FOREIGN PATENT DOCUMENTS

| | | | |
|---|---|---|---|
| AU | 2002256254 B2 | 5/2007 | |
| AU | 2007201246 A1 | 3/2009 | |

(Continued)

OTHER PUBLICATIONS

Sallam et al., Systematic review: pathophysiology and management of gastrointestinal dysmotility in systemic sclerosis (scleroderma), Alimentary Pharmacology & Therapeutics 23, 2006, pp. 691-712. (Year: 2006).*
Savarino et al., Gastrointestinal motility disorder assessment in systemic sclerosis, Rheumatology, 2013; 52, pp. 1095-1100. (Year: 2013).*
Suliman et al., Anti-Vinculin Antibodies: A Novel Biomarker in Systemic Sclerosis, and Its Association with Vascular Involvement, Meeting: 2016 ACR/ARHP Annual Meeting, 2016, retrieved from: https://acrabstracts.org/abstract/anti-vinculinantibodies-a-novel-biomarker-in-systemic-sclerosis-and-its-association-with-vascular-involvement/.

(Continued)

*Primary Examiner* — Gary Counts
(74) *Attorney, Agent, or Firm* — Linda B. Huber; Nixon Peabody LLP

(57) ABSTRACT

Described herein are methods of diagnosing systemic sclerosis (SSc) involving the detection of anti-vinculin antibodies. Also described herein are methods of selecting treatment of subjects diagnosed with systemic sclerosis (SSc), and methods of treating systemic sclerosis (SSc).

8 Claims, 1 Drawing Sheet
Specification includes a Sequence Listing.

(56) References Cited

U.S. PATENT DOCUMENTS

| | | |
|---|---|---|
| 2011/0294726 A1 | 12/2011 | Pimentel et al. |
| 2012/0088257 A1 | 4/2012 | Mouthon et al. |
| 2013/0331283 A1 | 12/2013 | Mcandrew et al. |
| 2014/0206636 A1 | 7/2014 | Lin et al. |
| 2015/0233944 A1* | 8/2015 | Pimentel ............ G01N 33/6887 514/18.3 |
| 2016/0103136 A1 | 4/2016 | Pimentel |
| 2017/0095543 A1 | 4/2017 | Lin et al. |
| 2018/0088130 A1 | 3/2018 | Pimentel et al. |
| 2018/0196063 A1 | 7/2018 | Pimentel et al. |
| 2018/0231551 A1 | 8/2018 | Pimentel et al. |
| 2018/0364255 A1 | 12/2018 | Pimentel et al. |
| 2019/0086406 A1* | 3/2019 | Chowdhury ..... G01N 33/56983 |
| 2019/0178890 A1 | 6/2019 | Pimentel et al. |
| 2019/0187153 A1 | 6/2019 | Pimentel et al. |
| 2019/0352375 A1* | 11/2019 | Saczynska ........... C07K 14/005 |
| 2020/0271665 A1 | 8/2020 | Pimentel et al. |
| 2020/0284804 A1 | 9/2020 | Pimentel et al. |
| 2021/0405046 A1 | 12/2021 | Pimentel et al. |

FOREIGN PATENT DOCUMENTS

| | | |
|---|---|---|
| AU | 2010213773 B2 | 10/2014 |
| AU | 2010213708 B2 | 12/2015 |
| AU | 2014331841 A2 | 3/2016 |
| AU | 2015330872 A1 | 4/2017 |
| AU | 2016201529 | 6/2018 |
| AU | 2013315981 B2 | 4/2019 |
| AU | 2014331841 | 6/2020 |
| BR | PI1008058-9 A8 | 3/2016 |
| BR | 112016007474-2 A2 | 9/2017 |
| CA | 2923651 A1 | 4/2015 |
| CA | 2962493 A1 | 4/2016 |
| CA | 2444548 C | 6/2016 |
| CA | 2922728 C | 2/2019 |
| CL | 1943-2011 | 2/2012 |
| CL | 2011-1944 | 2/2012 |
| CL | 2016000820 A1 | 9/2016 |
| CN | 105744956 A1 | 7/2016 |
| CN | 107003308 A | 8/2017 |
| CO | 16091069 | 9/2016 |
| DE | 602013027637.4 | 10/2017 |
| EP | 1 385 476 | 2/2004 |
| EP | 2 261 665 B1 | 6/2004 |
| EP | 1 200 828 B1 | 10/2007 |
| EP | 2 261 664 A2 | 12/2010 |
| EP | 2 305 213 A2 | 4/2011 |
| EP | 1 811 303 B1 | 6/2011 |
| EP | 2396029 | 12/2011 |
| EP | 2 256 498 B1 | 4/2015 |
| EP | 2 895 856 | 7/2015 |
| EP | 2 267 445 B1 | 8/2016 |
| EP | 3054977 A1 | 8/2016 |
| EP | 3204771 A1 | 8/2017 |
| EP | 2396652 B | 12/2017 |
| EP | 3349004 | 7/2018 |
| EP | 1385476 B1 | 1/2021 |
| EP | 3054977 B1 | 7/2021 |
| IL | 251606 A | 12/2020 |
| IN | 201727012044 A | 6/2017 |
| JP | 2009-102401 | 5/2009 |
| JP | 4653936 | 12/2010 |
| JP | 2017502253 A | 1/2017 |
| JP | 2017531801 A | 10/2017 |
| JP | 6784669 B2 | 10/2020 |
| KR | 20160062161 A | 6/2016 |
| KR | 20170067795 A | 6/2017 |
| KR | 10-2203568 B1 | 1/2021 |
| KR | 102259588 B1 | 5/2021 |
| KR | 102426541 B1 | 7/2022 |
| MX | 2015-048142 | 7/2015 |
| MX | 2016004167 A | 6/2016 |
| MX | 348670 | 6/2017 |
| MX | 2017055077 | 7/2017 |
| MX | 2017-045632 | 11/2017 |
| NZ | 717633 A | 11/2021 |
| NZ | 730490 A | 11/2021 |
| PE | 08822016 A1 | 9/2016 |
| RU | 2397178 C1 | 8/2010 |
| RU | 2683781 C2 | 4/2019 |
| RU | 2706361 C2 | 11/2019 |
| SG | 11201601733 A | 5/2018 |
| SG | 11201702395 W | 3/2021 |
| WO | WO 92/06690 A1 | 4/1992 |
| WO | WO 01/11077 A2 | 2/2001 |
| WO | WO 01/11334 A2 | 2/2001 |
| WO | WO 2002/083926 A2 | 10/2002 |
| WO | WO 2004/024097 A2 | 3/2004 |
| WO | WO 2005/029091 A2 | 3/2005 |
| WO | WO 2006/102536 A2 | 9/2006 |
| WO | WO 2008/016708 A2 | 2/2008 |
| WO | WO 2009/108814 A1 | 9/2009 |
| WO | WO 2010/093776 A1 | 8/2010 |
| WO | WO 2010/093801 A1 | 8/2010 |
| WO | WO 2012/007913 A2 | 1/2012 |
| WO | WO 2014/042828 A2 | 3/2014 |
| WO | WO 2015/054529 A1 | 4/2015 |
| WO | WO 2016/057772 A1 | 4/2016 |
| WO | WO 2018/140869 A1 | 8/2018 |

OTHER PUBLICATIONS

Riddle et al., Persisting Consequence of Intestinal Infection: Summary of the Seminar, 2014, Old Herborn University Seminar No. 7, pp. 125-137.

Villano et al., Systemic sclerosis sera affect fibrillin-1 deposition by dermal blood microvascular endothelial cells: therapeutic implications of cyclophosphamide, Arthritis Research & Therapy, 2013(15), pp. 1-12.

Beppu et al., Autoantibodies against vinculin in patients with chronic inflammatory demyelinating polyneuropathy, Journal of Neuroimmunology, 2015, pp. 9-15.

Virandera et al., Antibodies to Cytolethal Distending Toxin B and Auto-Antibodies to Human Vinculin Are Elevated in BS Subjects, Gastroenterology, 2013, vol. 144(5), Abstract.

Morales et al., SA2024 Antibodies to an 18-Residue Peptide of Cdt Are Found in the Serum of Rats in a Model of Post-Infectious IBS, 2011, Gastroenterology, vol. 140(5), Suppl. 1, p. S-371.

Jayne, The diagnosis of vasculitis, Best Practice & Research Clinical Rheumatology, 2009, vol. 23(3), pp. 445-453.

Supplementary European Search Report for EP 18744324 dated Oct. 21, 2020, 8 pages.

PCT/US2010/023873 International Search Report and Written Opinion dated Apr. 1, 2010; 7 pages.

PCT/US2010/023873 International Preliminary Report on Patentability dated Aug. 16, 2011; 6 pages.

PCT/US2013/005626 International Search Report and Written Opinion dated Aug. 18, 2014; 14 pages.

PCT/US2013/005626 International Preliminary Report on Patentability dated Aug. 18, 2014; 12 pages.

PCT/US2010/023911 International Search Report and Written Opinion dated May 14, 2010; 11 pages.

PCT/US2010/023911 International Preliminary Report on Patentability dated Aug. 16, 2011; 8 pages.

PCT/US2014/059957 International Search Report and Written Opinion dated Jan. 8, 2015; 11 pages.

PCT/US2014/059957 International Preliminary Report on Patentability dated Apr. 21, 2016; 9 pages.

PCT/US2015/054655 International Search Report and Written Opinion dated Feb. 12, 2016; 7 pages.

International Search Report and Written Opinion of PCT/US2018/015723, Dated Apr. 24, 2018, 13 Pages.

Extended European Search Report of EP 15849701.6 Dated Feb. 8, 2018, 10 Pages.

EP Application No. 17206465.1 Extended Search Report dated Apr. 20, 2018.

EP Application No. 10741728.9 Extended Search Report dated Oct. 17, 2014; 7 pages.

(56) References Cited

OTHER PUBLICATIONS

EP Application No. 13837424.4 Extended Search Report dated May 9, 2016; 8 pages.
EP Application No. 10741713.1 Extended Search Report dated Jul. 27, 2012, 16 Pages.
EP Application No. 14851688.3 Extended Search Report dated Mar. 10, 2017; 10 pages.
Written Opinion of Singapore Application No. 11201601733V, dated Apr. 17, 2017; 8 pages.
Written Opinion of Singapore Application No. 11201702395W, dated Nov. 24, 2017, 8 pages.
Office Action of RU 2016116766, dated Jul. 25, 2018, 12 Pages.
Abuoun et al. Cytolethal Distending Toxin (CDT)-Negative Campylobacter jejuni Strains and Anti-CDT Neutralizing Antibodies are Induced during Human Infection but Not during Colonization in Chickens. Infection and Immunity (2005). 73(5): 3053-3062.
American College of Gastroenterology Task Force On Ibs. An Evidence-Based Position Statement on the Management of Irritable Bowel Syndrome. The American Journal of Gastroenterology (2009). 104(S1): S1-35.
Air et al. Mechanism of Antigenic Variation in an Individual Epitope on Influenza Virus N9 Neuraminidase. Journal of Virology (1990). 64(12):5797-5803.
Bourke, B. Campylobacter infection: small bowel and colon. Current Opinion in Gastroenterology. (2002). 18:4-9.
Bradesi et al., Novel Therapeutic Approaches in IBS, Current Opinion in Pharmacology, 2007, vol. 7(6), pp. 598-604.
Cambridge et al. Anti-neutrophil antibodies in inflammatory bowel disease: prevalence and diagnostic role. Gut (2013). 33:668-674.
Carey et al. A prospective evaluation of the pathogenesis of detrusor instability in woman, using electron microscopy and immunohistochemistry. BJU International (2000). 86:970-976.
Colman, PM. Effects of amino acid sequence changes on antibody-antigen interactions. Res Immunol (1994). 145(1):33-6.
Connor, B. Sequelae of Traveler's Diarrhea: Focus on Postinfectious Irritable Bowel Syndrome. Clinical Infectious Diseases (2005). 41(suppl 3):S577-S586.
Costello et al., The Effect of an Elemental Diet on Stool Output in Irritable Bowel Syndrome, 1994, Proceedings of the Nutrition Society, vol. 53(3), p. 223A.
Dib et al., Targets of Anti-Endothelial Cell Antibodies in Pulmonary Hypertension and Scleroderma, 2012, Eur. Respir. J., vol. 39, pp. 1405-1414.
Dunlop et al. Relative Importance of Enterochromaffin Cell Hyperplasia, Anxiety, and Depression in Postinfectious IBS. Gastroenterology (2003). 125:1651-1659.
Dupont, H. Postinfectious Irritable Bowel Syndrome: Clinical Aspects, Pathophysiology, and Treatment. Practical Gastroenterology (2007). 31(S9): 18-24.
Dupont, A. et al. Travelers' Diarrhea: Modern Concepts and New Developments. Current Treatment Option in Gastroenterology. Database Medline: US National Library of Medicine. (2006). Abstract Only.
Fox et al. Gastroenteritis in NF-kappaB-deficient mice is produced with wildtype Camplyobacter jejuni but not with C. jejuni lacking cytolethal distending toxin despite persistent colonization with both strains. Infection & Immunity (2004). 72(2):1116-25.
Halsey, J. Current and Future Treatment Modalities for Clostridium-difficile-Associated Disease. Am J. Health-Syst Pharm (2008). 65:705-715.
Hickey et al. Campylobacter jejuni Cytolethal Distending Toxin Mediates Release of Interleukin-8 from Intestinal Epithelial Cells. Infection and Immunity (2000). 68(12):6535-6541.
Jee et al. Antibotics and Cdt Expression in Campylobacter Jejuni Contribute to Duration of Colonization in Rats. Gastroenterology. (2008). 134(4). Abstract Only.
Jee et al., ICC Density Predicts Bacterial Overgrowth in a Rat Model of Post-Infectious IBS, 2010, World J. Gastroenterol, vol. 16(29), pp. 3680-3686.
Johnson et al. Interruption of Recurrent Clostridium difficle-Associated Diarrhea Episodes by Serial Therapy with Vancomycin and Rifaximin. Clinical Infectious Diseases (2007). 44:846-848.
Kokkotou et al. Comparative Efficacies of Rifaximin and Vancomycin for Treatment of Clostridium difficile-Associated Diarrhea and Prevention of Disease Recurrence in Hamsters. Antimicrobial Agents and Chemotherapy (2008). 52(3): 1121-1126.
Lembo et al. Use of serum biomarkers in a diagnostic test for irritable bowel syndrome. Alimentary Pharmacology & Therapeutics (2009). 29:834-842.
Mariuzza et al. The structural basis of antigen-antibody recognition. Annu Rev Biophys Biophys Chem (1987). 16:139-59. Abstract Only.
Medindia. IBS Sufferers Benefited by Non-Absorbable Antibiotics. (2006). Retrieved from Internet: www.medindia.net/news/view_newsmain.asp?x=15225.
Morales et al. Antibodies to Cytolethal Distending Toxin of Campylobacter Jejuni Bind to Enteric Neuronal Elements: Further Evidence for Molecular Mimicry. Gastroenterology (2012). 142(5): Suppl 1.
Morales et al. Effect of Rifaximin Treatment on Anti-Vinculin Antibodies in IBS with Diarrhea. Gastroenterology (2016).150(4). Supplement 1. p. S-695.
Morales et al. Tu2056 Antibodies to Cytolethal Distending Toxin B and Auto-Antibodies to Human Vinculin are Elevated in IBS Subjects. Gastroenterology (2013). 144(5): Suppl. 1, p. S-914.
Moss-Morris et al. To "Lump" or to "Split" the Functional Somatic Syndromes: Can Infections and Emotional Risk Factors Differentiate between the Onset of Chronic Fatigue Syndrome and Irritable Bowel Syndrome. Psychosomatic Medicine (2006). 68:463-469.
Neal et al. Prevalence of Gastrointestinal Symptoms Six Months after Bacterial Gastroenteritis and Risk Factors for Development of the Irritable Bowel Syndrome: Postal Survey of Patients. BMJ (1997). 314:779, 14 pages.
Nelson et al. Vinculin Activators Target Integrins from within the Cell to Increase Melanoma Sensitivity to Chemotherapy. Molecular Cancer Research (2011). 9(6):1-12.
Nemeth et al. Altered Cytoskeleton in Smooth Muscle of Aganglionic Bowel. Arch Pathol Lab Med (2002). 126:692-696.
Novak, K. A Serologic Test for Irritable Bowel Syndrome and Other News from ACG. Gastroenterology Press Highlights (2013); pp. 1-2. Retrieved from: <www.gastrojournal.org/pb/assets/raw/Health%20Advance/journals/ygast/November26_Pres sHighlight3.pdf> on Feb. 3, 2016.
Pandey et al., Association of Cytolethal Distending Toxin Locus cdtB with Enteropathogenic Escherichia coli Isolated from Patients with Acute Diarrhea in Calcutta, India, 2003, J. Clin. Microbiol., vol. 41(11), pp. 5277-5281.
Peng et al. a-Catenin Uses a Novel Mechanism to Activate Vinculin. The Journal of Biological Chemistry (2012). 287(10): 7728-7737.
Pimentel, Mark, Evaluating a bacterial hypothesis in IBS using a modification of Koch's postulates: part 1, 2010, Am J Gastroenterol, vol. 105, pp. 718-721.
Pimentel et al. A New Rat Model Links Two Complementary Theories in Irritable Bowel Syndrome. Digestive Diseases and Sciences (2007). 53(4):982-989.
Pimentel et al. Anti-vinculin antibodies: Multicenter validation of a diagnostic blood test for irritable bowel syndrome. The American Journal of Gastroenterology (2013). 108:1887; p. S571. Abstract Only.
Pimentel et al. Autoimmunity to vinculin in humans may be important in the pathophysiology of IBS. Gastroenterology (2014). 146(5); suppl 1, Su2020. Abstract Only.
Pimentel et al. Development and Validation of a Biomarker for Diarrhea-Predominant Irritable Bowel Syndrome in Human Subjects. PLoS One (2015). 10(5): pp. 1-12.
Purdy et a. Characterisation of cytolethal distending toxin (CDT) mutants of Campylobacter jejuni. J. Med. Microbiol. (2000). 49: pp. 473-479.
Regent et al., Identification of Target Antigens of Anti-Endothelial Cell and Anti-Vascular Smooth Muscle Cell Antigodies in Patients with Giant Cell Arteritis: a Proteomic Approach, 2011, Arthritis Research & Therapy, 13: R107, 15 Pages.

(56) References Cited

OTHER PUBLICATIONS

Rezaie et al. Assessment of Anti-Vinculin and Anti-CdtB Antibodies in IBS Subtypes. Gastroenterology (2016).150(4). Supplement 1. p. S62.

Rezaie et al. Assessment of Anti-Vinculin and Anti-Cytolethal Distending Toxin B Antibodies in Subtypes of Irritable Bowel Syndrome, 2017, Digestive Diseases and Sciences, vol. 62(6), pp. 1480-1485.

Rolle et al. Structural basis of voiding dysfunction in megacystis microcolon intestinal hypoperistalsis syndrome. Journal of Pediatric Urology (2006). 2:277-284.

Sabota et al. A New Variant of Food Poisoning: Enteroinvasive Klebsiella Pneumoniae and *Escherichia coli* Sepsis from a Contaminated Hamburger. The American Journal of Gastroenterology (1998). 93(1): 118-119.

Science Daily. Irritable Bowel Syndrome Study Shows that Targeted Antibiotics Lead to Long-Lasting Improvement in Symptoms. (2005). Retrieved from Internet: http://www.sciencedaily.com/releases/2005/11/051109181127.htm.

Spiller et al. Increased rectal mucosal enteroendocrine cells, T lymphocytes, and increased gut permeability following acute Campylobacter enteritis and inpost-dysenteric irritable bowel syndrome. Gut (2000). 47:804-811.

Suh et al. Patients with irritable bowel syndrome or constipation have an increased risk for ischaemic colitis. Alimentary Pharmacology & Therapeutics (2007). 25:681-692.

Sung et al. Antibody to Cytolethal Distending Toxin of Campylobacter Jejuni Stains Small Bowel Myenteric Neuromuscular Elements in Control and C. Jejuni Exposed Rats: A Possible Role of Molecular Mimicry. Gastroenterology (2010). 138(5). p. S-770.

Taylor et al. Rifaximin, a Nonabsorbed Oral Antibiotic, Prevents Shigellosis after Experimental Challenge. Clinical Infectious Diseases. (2006). 42:1283-1288.

The Free Dictionary. Definition of Mitigation by the Free Online Dictionary, Thesaurus and Encyclopedia. Retrieved from: www.thefreedictionary.com/p/mitigation on Nov. 19, 2013.

Trees et al. Genome Sequences of 228 Shiga Toxin-Producing Escherichia coli Isolates and 12 Isolates Representing Other Diarrheagenic *E. coli* Pathotypes. Genome Announc (2014). 2(4): 3 pages.

Triantafyllou et al. Evaluating the Role of Cytolethal Distending Toxin in the Development of Small Intestinal Bacterial Overgrowth in a Rat Model Post-Infectious IBS. Gastroenterology (2014). 146(5): suppl 1, Sul424. Abstract Only.

Turkay et al. Noninvasive Methods in Evaluation of Inflammatory Bowel Disease: Where Do We Stand Now? An Update. Clinics (2010). 65(2):221-31.

Weller et al., Complete Sequence of Human Vinculin and Assignment of the Gene to Chromosome 10, 1990, Proceedings of the National Academy of Sciences of the USA, vol. 87, pp. 5667-5671.

Vasculitis Symptoms and Causes, Mayo Clinic, 2021, retrieved from the internet: https://www.mayoclinic.org/diseases-conditions/vasculitis/symptoms-causes/syc-20363435>, pp. 1-3.

Notice of Allowance for U.S. Appl. No. 16/877,230 dated May 23, 2023, 15 pages.

\* cited by examiner

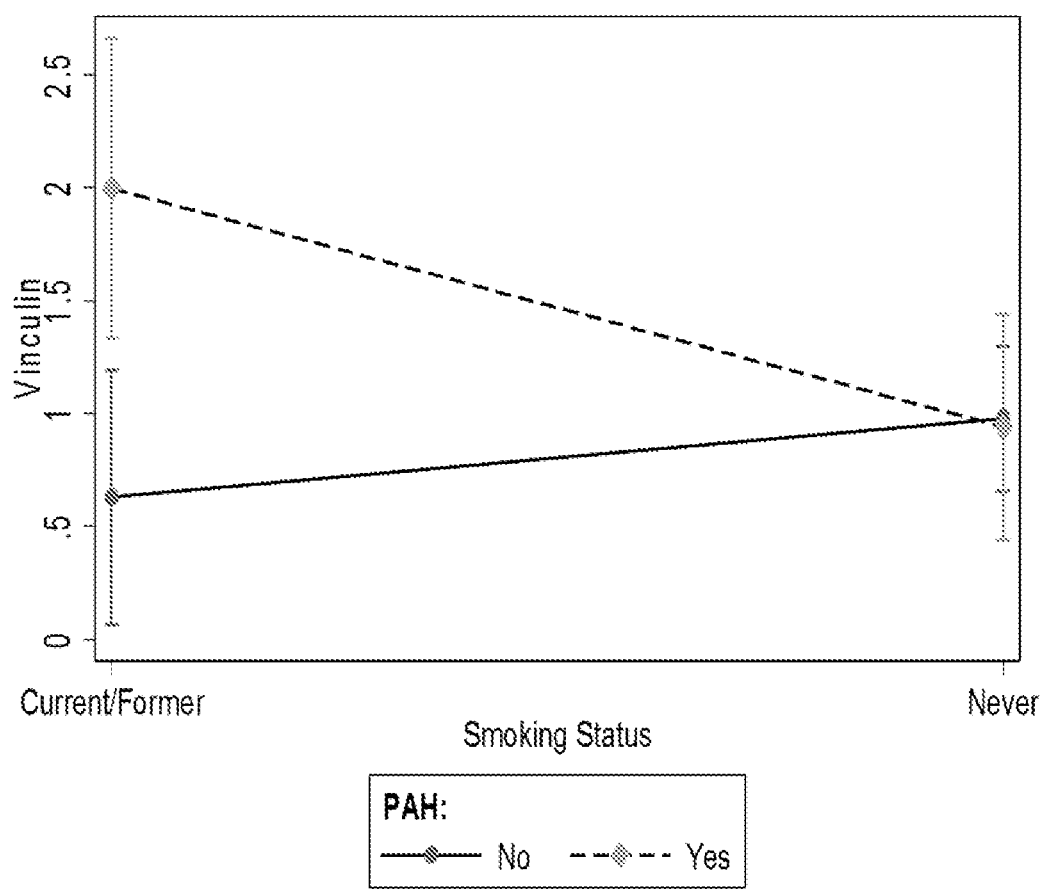

DIAGNOSIS OF SCLERODERMA

CROSS-REFERENCE TO RELATED APPLICATIONS

This application is a National Phase of International Application No. PCT/US2018/015723 filed Jan. 29, 2018, currently pending, which designated the U.S. and that International Application was published under PCT Article 21 (2) in English, which also includes a claim of priority under 35 U.S.C. § 119 (e) to U.S. provisional patent application No. 62/451,923 filed Jan. 30, 2017, the entirety of which is hereby incorporated by reference.

FIELD OF INVENTION

This invention relates to the measurement of anti-vinculin antibodies in subjects who have systemic sclerosis or who are suspected to have systemic sclerosis. The invention also relates to the diagnosis and treatment of systemic sclerosis.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

This invention relates to the scleroderma. Systemic sclerosis (SSc) (also known as systemic scleroderma) is a chronic connective tissue disease generally classified as an autoimmune disease. Systemic sclerosis can involve the skin, esophagus, gastrointestinal tract (stomach and bowels), lungs, kidneys, heart and other internal organs. It can also affect blood vessels, muscles and joints. Gastrointestinal (GI) dysmotility is a commonly encountered challenge in most patients with systemic sclerosis (SSc). It has a major impact on their quality of life, and morbidity in SSc. Currently proposed etiopathogenic mechanisms fail to fully explain the various phenotypic presentations of GI involvement in SSc patients.

Thus, there remains a need in the art to identify the cause and methods to diagnose and treat systemic sclerosis.

SUMMARY OF THE INVENTION

The following embodiments and aspects thereof are described and illustrated in conjunction with compositions and methods which are meant to be exemplary and illustrative, not limiting in scope.

Various embodiments provide for a method for diagnosing systemic sclerosis, comprising: obtaining a biological sample from a subject who desires a diagnosis regarding systemic sclerosis; detecting a level of anti-vinculin antibodies in the biological sample; and diagnosing systemic sclerosis when the level of anti-vinculin antibodies is higher than a reference level of anti-vinculin antibodies.

In various embodiments, the subject can exhibit one or more symptoms of systemic sclerosis. In various embodiments, the biological sample can be whole blood, serum, or plasma. In various embodiments, detecting the level of anti-vinculin antibodies can comprise using an enzyme-linked immunosorbent assay (ELISA). In various embodiments, detecting the level of anti-vinculin antibodies can comprise using immunohistochemistry, flow cytometry, fluorescence in situ hybridization (FISH), radioimmuno assay, or affinity purification. In various embodiments, the anti-vinculin antibodies can be capable of binding specifically to an epitope on vinculin or SEQ ID NO:1. In various embodiments, vinculin or a fragment thereof can be used to detect the anti-vinculin antibodies. In various embodiments, the method can further comprise diagnosing pulmonary artery hypertension (PAH) when the level of anti-vinculin antibodies is higher than a reference level of anti-vinculin antibodies.

Various embodiments of the present invention provide for a method of measuring the level anti-vinculin antibodies in a subject who has systemic sclerosis or has one or more symptoms of systemic sclerosis, comprising: measuring a level of anti-vinculin antibodies in a biological sample obtained from the subject who has systemic sclerosis or has one or more symptoms of systemic sclerosis by using vinculin or a fragment thereof to assay the biological sample. In various embodiments, vinculin or a fragment thereof can be SEQ ID NO:1 or a fragment thereof. In various embodiments, measuring the level of anti-vinculin antibodies can comprise using enzyme-linked immunosorbent assay (ELISA). In various embodiments, the biological sample can be whole blood, serum, or plasma. In various embodiments, measuring the level of anti-vinculin antibodies can comprise using immunohistochemistry, flow cytometry, fluorescence in situ hybridization (FISH), radioimmuno assay, or affinity purification.

Various embodiments of the present invention provide for a system, comprising: a biological sample obtained from a subject who has systemic sclerosis or has one or more symptoms of systemic sclerosis; and an assay to measure a level of anti-vinculin antibodies in the biological sample. In various embodiments, the assay comprises vinculin or a fragment thereof.

Various embodiments provide for a method of selecting a therapy for systemic sclerosis, comprising: measuring a level of anti-vinculin antibodies by a method of the present invention and selecting a therapy for systemic sclerosis to treat systemic sclerosis when the level of anti-vinculin antibodies is higher than a reference value.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIG. 1 depicts the interaction of pulmonary artery hypertension (PAH) and smoke on vinculin in accordance with various embodiments of the present invention.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular*

*Biology* 3rd *ed., Revised*, J. Wiley & Sons (New York, NY 2006); March, *Advanced Organic Chemistry Reactions, Mechanisms and Structure* 7th *ed.*, J. Wiley & Sons (New York, NY 2013); and Sambrook and Russel, *Molecular Cloning: A Laboratory Manual* 4th *ed.*, Cold Spring Harbor Laboratory Press (Cold Spring Harbor, NY 2012), provide one skilled in the art with a general guide to many of the terms used in the present application. For references on how to prepare antibodies, see D. Lane, *Antibodies: A Laboratory Manual* 2nd *ed.* (Cold Spring Harbor Press, Cold Spring Harbor NY, 2013); Kohler and Milstein, (1976) Eur. J. Immunol. 6: 511; Queen et al. U.S. Pat. No. 5,585,089; and Riechmann et al., Nature 332: 323 (1988); U.S. Pat. No. 4,946,778; Bird, Science 242:423-42 (1988); Huston et al., Proc. Natl. Acad. Sci. USA 85:5879-5883 (1988); Ward et al., Nature 334:544-54 (1989); Tomlinson I. and Holliger P. (2000) Methods Enzymol, 326, 461-479; Holliger P. (2005) Nat. Biotechnol. September; 23(9):1126-36).

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Mammal" as used herein refers to any member of the class Mammalia, including, without limitation, humans and nonhuman primates such as chimpanzees, and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus adult and newborn subjects, as well as fetuses, whether male or female, are intended to be including within the scope of this term.

"Treatment" and "treating," as used herein refer to both therapeutic treatment and prophylactic or preventative measures (e.g., to reduce the likelihood of having the condition or disease condition), wherein the object is to prevent or slow down (lessen) the targeted pathologic condition or disorder even if the treatment is ultimately unsuccessful. Those in need of treatment include those already with the condition or disorder as well as those prone to have the condition or disorder or those in whom the condition or disorder is to be prevented (e.g., reducing the likelihood of having the condition or disorder).

"Antibody" or "antibodies" as used herein include polyclonal antibodies, monoclonal antibodies, antibody variants such as single chain (recombinant) Fv, human antibodies, humanized antibodies, chimeric antibodies, and immunologically active fragments of antibodies.

"Binds specifically" as used herein refers to the act of an antibody binding to its antigen and is intended to exclude low-level, non-specific binding that may occur between random proteins. "Binds specifically" as used herein is not intended and does not imply that the antibody will not bind to any protein other than the proteins or polypeptides as disclosed herein since antibodies can cross-react with any protein that includes the relevant epitope.

"Significantly higher" as used herein relating to reference amounts refers to a statistically significant amount higher than the reference amount.

Small intestinal bacterial overgrowth (SIBO) is common in SSc, reported at a prevalence of 30%-62%. A potential contribution of SIBO to the pathogenesis of another motility disorder (irritable bowel syndrome (IBS)) has been investigated and a significant role of microbes and their toxins (CdtB) has been identified by the inventor. Anti-CdtB antibodies were reported to cross-react with vinculin in interstitial cell of Cajal (ICC) and myenteric ganglia, required for normal gut motility. Vinculin, in turn was shown to be over-expressed in endothelial cells and may have a role in the impaired angiogenic process seen in SSc. While not wishing to be bound by any particular theory, the inventors believed that overexpression of vinculin in SSc triggers anti-vinculin antibodies which contributes to both GI involvement and vasculopathic changes in SSc.

Described herein, the inventor found the presence of anti-vinculin antibodies in SSc patients, and their relation with pulmonary artery hypertension not GI involvement.

Vinculin is a 117-kDa cytoplasmic actin-binding protein that is a key component of both focal adhesions and adherens junctions, forming the link between integrins or cadherins respectively and the actin cytoskeleton.

Various embodiments of the present invention are based, at least in part, on these findings.

Methods of Diagnosing Systemic Sclerosis

Various embodiments of the present invention provide for methods, assays and systems for diagnosing systemic sclerosis.

In various embodiments, the method comprises obtaining a biological sample from a subject desiring a diagnosis regarding systemic sclerosis, detecting a level of anti-vinculin antibodies in the biological sample, and making a diagnosis of systemic sclerosis if the level of anti-vinculin antibodies is higher than a reference value. In some embodiments, the method further comprises diagnosing pulmonary artery hypertension (PAH) when the level of anti-vinculin antibodies is higher than a reference level of anti-vinculin antibodies. Reference value of anti-vinculin antibodies that can be used are described herein.

In various embodiments, the method comprises obtaining a biological sample from a subject desiring a diagnosis regarding systemic sclerosis; detecting a presence or absence of anti-vinculin antibodies in the biological sample, and making a diagnosis of systemic sclerosis if the presence of anti-vinculin antibodies is detected. In some embodiments, the method further comprises diagnosing pulmonary artery hypertension (PAH) when the presence of anti-vinculin antibodies is detected. In certain embodiments, the method further comprises selecting a systemic sclerosis treatment if systemic sclerosis is diagnosed.

In various embodiments, the method comprises detecting the presence or absence of anti-vinculin antibodies in a biological sample from a subject, wherein the presence of the anti-vinculin antibodies indicates the presence of systemic sclerosis. In some embodiments, the method further comprises diagnosing pulmonary artery hypertension (PAH) when the level of anti-vinculin antibodies is higher than a reference level of anti-vinculin antibodies. In various embodiments, the subject is one who desires a diagnosis regarding systemic sclerosis.

In various embodiments, if a diagnosis or suspicion of systemic sclerosis is made, it can be further correlated with one or more symptoms of systemic sclerosis or PAH to further confirm systemic sclerosis or PAH. For example, it can be correlated with 2, 3, 4, 5, 6, 7, 8, 9, or 10 symptoms of systemic sclerosis, or with 2, 3, 4, or 5 symptoms of PAH; or 5, 10, 15, 20 or more symptoms of systemic sclerosis. Symptoms of systemic sclerosis and PAH can be those as described herein.

Various embodiments provide for a method of detecting the presence or absence of anti-vinculin antibodies in a subject who has systemic sclerosis or has one or more symptoms of systemic sclerosis. In various embodiments, the method comprises detecting a presence or absence of anti-vinculin antibodies in a biological sample obtained from the subject who has systemic sclerosis or has one or more symptoms of systemic sclerosis by using vinculin or a fragment thereof to assay the biological sample.

Various embodiments provide for a method of measuring the level anti-vinculin antibodies in a subject who has systemic sclerosis or has one or more symptoms of systemic sclerosis. In various embodiments, the method comprises measuring a level of anti-vinculin antibodies in a biological sample obtained from the subject who has systemic sclerosis or has one or more symptoms of systemic sclerosis by using vinculin or a fragment thereof to assay the biological sample.

Various embodiments provide for a method of determining whether a level anti-vinculin antibodies in a subject who has systemic sclerosis or has one or more symptoms of systemic sclerosis is higher than a reference level. In various embodiments, the method comprises measuring a level of anti-vinculin antibodies in a biological sample obtained from the subject who has systemic sclerosis or has one or more symptoms of systemic sclerosis by using vinculin or a fragment thereof to assay the biological sample; and determining if the level of anti-vinculin antibodies is higher than a reference level.

Prior to the present invention, there would not be a reason to detect for the presence or absence of anti-vinculin antibodies, to measure the anti-vinculin antibody levels, or to determine if anti-vinculin antibodies are higher than a reference level in these subjects. As such one of ordinary skill in the art would not be performing the present invention on a subject who has systemic sclerosis or has one or more symptoms of systemic sclerosis.

Systems for Diagnosing Systemic Sclerosis

In various embodiments, the system comprises an isolated biological sample from a subject desiring a diagnosis regarding systemic sclerosis, and an assay for detecting a presence or absence of an anti-vinculin antibody or a level of anti-vinculin antibody in the biological sample to diagnose systemic sclerosis.

Prior to the present invention, there would not be a reason to detect for the presence or absence of anti-vinculin antibodies, to measure the anti-vinculin antibody levels, or to determine if anti-vinculin antibodies are higher than a reference level in a subject who has systemic sclerosis or has one or more symptoms of systemic sclerosis. As such one of ordinary skill in the art would not have looked for such a system.

Assays

In various embodiments, various assays are used to detect a presence or absence of an anti-vinculin antibody or to determine the level of anti-vinculin antibody in the biological sample.

In various embodiments, the assay used in the present invention is an enzyme-linked immunosorbent assay (ELISA), including but not limited to indirect ELISA, sandwich ELISA, competitive ELISA, multiple and portable ELISA.

In various embodiments, the assay comprises a first reagent to react with the biological sample if the biological sample comprises the anti-vinculin antibody (if anti-vinculin antibodies are not present, then the first reagent will not react the biological sample, but the first reagent is still present in the assay), a second reagent (e.g., secondary antibody) to react with the anti-vinculin antibody or a second reagent to react with the first reagent, and a substrate. In various embodiments, the first reagent is vinculin or a fragment thereof. In various embodiments, the second reagent comprises a label to produce a signal to indicate the presence of the anti-vinculin antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the label is an enzyme that will react with the substrate. In various embodiments, the first reagent is on a solid phase (e.g., plate, multi-well plate).

In various embodiments, the assay comprises a first reagent to react with the anti-vinculin antibody. In various embodiments, the first reagent comprises a label to produce a signal to indicate the presence of the anti-vinculin antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the reagent is on a solid phase (e.g., plate, multi-well plate).

In various embodiments, the system further comprises a machine for determining a presence of systemic sclerosis if the presence of anti-vinculin antibodies is detected, or determining the absence of systemic sclerosis if there is an absence of anti-vinculin antibodies. In various embodiments, the machine is a computer. In various embodiments, the computer comprises a display element for displaying whether the patient has systemic sclerosis.

In various embodiments, the assay comprises using vinculin or a fragment thereof to detect the levels of the anti-vinculin antibodies. For example, determining the presence or level of anti-vinculin antibodies comprises contacting vinculin or a fragment thereof as discussed herein to a biological sample from a subject desiring a determination regarding systemic sclerosis, wherein the anti-vinculin antibody (if present in the biological sample) specifically binds to the vinculin or the fragment thereof; measuring the levels the anti-vinculin antibodies in the biological sample; and identifying that the subject has systemic sclerosis if the levels of the anti-vinculin antibodies higher than a reference value. Vinculin and fragments of vinculin are further described herein.

In various embodiments, detecting the presence or absence of the antibody is performed on a biological sample obtained from the subject. In another embodiment, detecting the presence or absence of the antibody is performed on a blood, serum, or stool sample obtained from the subject. One of ordinary skill in the art will readily appreciate methods and systems that can be used to detect the presence or absence of an antibody that binds specifically to vinculin, SEQ ID NO:1 or a fragment thereof. These methods and systems include but are not limited to ELISA, immunohistochemistry, flow cytometry, fluorescence in situ hybridization (FISH), radioimmuno assays, and affinity purification.

In various embodiments, vinculin, SEQ ID NO:1 or a fragment thereof (as described above) is used as a substrate, antigen, or reagent (e.g., collector, trap) to bind anti-vinculin antibodies (if present).

In certain embodiments, detecting the presence or absence of an antibody that binds specifically to vinculin, SEQ ID NO:1 or a fragment thereof may be performed by contacting vinculin, SEQ ID NO:1 or a fragment thereof to a biological sample obtained from the subject to isolate the antibody that binds specifically to vinculin, SEQ ID NO:1 or a fragment thereof, wherein the isolation of the antibody that binds specifically to vinculin, SEQ ID NO:1 or a fragment thereof indicates the presence of the antibody and the lack of isolation of the antibody that binds specifically to vinculin, SEQ ID NO:1 or a fragment thereof indicates the lack of the antibody. In various embodiments, the fragment of vinculin or SEQ ID NO:1 may be the fragments as described herein. As an example, an affinity matrix comprising vinculin, SEQ ID NO:1 or a fragment thereof can be bound to a solid support; the biological sample can be contacted to the affinity matrix to produce an affinity matrix-antibody complex (if the antibody is present); the affinity matrix-antibody complex can be separated from the remainder of the biological sample; and the antibody can be released from the affinity matrix. In another example, a label (e.g., fluorescent label) can be placed on vinculin, SEQ ID NO:1 or a fragment thereof; the labeled vinculin, SEQ ID NO:1 or a fragment thereof can be contacted with a biological sample to allow the antibody (if present) to bind specifically to the labeled vinculin, SEQ ID NO:1 or a fragment thereof. In various embodiments, the labeled vinculin, SEQ ID NO:1 or a fragment thereof can be separated out and analyzed for its binding to the antibody.

In various embodiments, when determining the presence or level of anti-vinculin antibodies, vinculin protein or a fragment thereof as described herein is used as the antigen at about 1.2 μg/ml concentration. In other embodiments, the concentration can be about 0.1, 0.2, 0.3, 0.4, 0.5, 0.6, 0.7, 0.8, 0.9, 1.0, 1.1., 1.3, 1.4, 1.5, 1.6, 1.7, 1.8, 1.9 or 2.0 μg/ml concentration. In various embodiments, an about 1:32 dilution of the biological sample (e.g., plasma) is used in the determination of the presence or level of anti-vinculin antibodies. In other embodiments, an about 1:8, 1:10, 1:12; 1:16, 1:20, 1:24, 1:30, 1:36, 1:48, or 1:64 dilution of the biological sample (e.g., plasma) is used in the determination of the presence or level of anti-vinculin antibodies. In other embodiments, an about 1:8 to 1:64 dilution of the biological sample (e.g., plasma) is used in the determination of the presence or level of anti-vinculin antibodies.

Antigens are immobilized for about 8, 9, 10, 11, 12, 13, 14, 15, 16, 17, 18, 19 or 20 hours (e.g., overnight, >16 hours) at about 4° C. onto high-binding plates (e.g., 96-well plates) in Borate Buffered Saline (BBS) at a pH of 8.2. Wells are alternately coated with antigen or left uncoated in BBS to allow determination of non-specific binding of plasma. Wells are blocked with about 3% bovine serum albumin in 1×PBS for about 1 hour at about room temperature. Coated and uncoated wells are then incubated with a 1:512 dilution of plasma for CdtB and a 1:32 dilution of plasma for vinculin for about 1 hour at room temperature. Antibodies to CdtB and vinculin are used as positive controls. This was followed by about 1 hour incubation with HRP conjugated secondary antibodies. Each step is followed by a series of washes using 0.05% PBS-Tween® 20. Finally, a 3,3',5,5'-Tetramethylbenzidine (TMB) substrate solution is used for visualization and immediately read on a plate reader (e.g., BioTek Synergy HT; Winooski, VT). The optical densities (OD) are read for about 90 minutes at 370 nm and used to compare levels of anti-vinculin. Raw OD values were used for the data analysis.

Selecting Treatments

Various embodiments provide for a method of selecting a therapy for systemic sclerosis for a subject in need thereof.

In various embodiments, the method comprises detecting the level of anti-vinculin antibodies in a subject who desires a diagnosis regarding systemic sclerosis; and selecting a therapy to treat systemic sclerosis when the level of anti-vinculin antibodies is higher than a reference value. In some embodiments, the method further comprises diagnosing pulmonary artery hypertension (PAH) when the level of anti-vinculin antibodies is higher than a reference level of anti-vinculin antibodies for PAH. Reference value of anti-vinculin antibodies that can be used are described herein.

In various embodiments, the method comprises: detecting the presence of anti-vinculin antibodies in a subject who desires a diagnosis regarding systemic sclerosis; and selecting a therapy to treat systemic sclerosis. In some embodiments, the method further comprises diagnosing pulmonary artery hypertension (PAH) when the level of anti-vinculin antibodies is higher than a reference level of anti-vinculin antibodies for PAH. Reference value of anti-vinculin antibodies that can be used are described herein.

Selecting a therapy as used herein, includes but is not limited to selecting, choosing, prescribing, advising, recommending, instructing, or counseling the subject with respect to the treatment.

In various embodiments, the method further comprises administering the therapy to treat systemic sclerosis. In various embodiments, the therapy is a therapy as described herein. In various embodiments, the therapy is an available therapy in the prior art.

In various embodiments, detecting the presence of anti-vinculin antibodies can be performed as described by the methods or systems of the present invention.

In various embodiments, the subject can be a subject presenting one or more symptoms of systemic sclerosis; for example, as discussed herein.

Methods of Treatments

Various embodiments provide for a method of treating systemic sclerosis in a subject in need thereof.

In various embodiments, the method comprises administering a systemic sclerosis treatment to a subject determined to have a level of anti-vinculin antibodies higher than a reference value.

In various embodiments, the method comprises detecting the level of anti-vinculin antibodies in a subject who desires a diagnosis regarding systemic sclerosis; and administering a systemic sclerosis therapy to treat systemic sclerosis when the level of anti-vinculin antibodies is higher than a reference value. Reference value of anti-vinculin antibodies that can be used are described herein.

In various embodiments, detecting level anti-vinculin antibodies can be performed as described by the methods or systems of the present invention.

In various embodiments, the subject can be a subject presenting one or more symptoms of systemic sclerosis; for example, as discussed herein.

Symptoms of Systemic Sclerosis

The subject described in the present invention can present with or have one or more symptom of system sclerosis. For example, the subject can have 3, 4, 5, 6, 7, 8, 9, or 10 symptoms of systemic sclerosis; or 5, 10, 15, 20 or more symptoms of systemic sclerosis.

Symptoms systemic sclerosis include, but are not limited to: constitutional (e.g., fatigue), musculoskeletal (e.g., arthritis, weakness, muscular pain), pulmonary (e.g., dyspnea, cough, pulmonary hypertension, emboli), cardiovascular (e.g., cardia failure, arrhythmias), GI (e.g., heartburn, dysphagia, malabsortion), renal (e.g., renal failure, hypertension), genitourinary (e.g., pregnancy with low birth weight infants), neurological (e.g., neuropathies, autonomic dysfunction), skin (e.g., tight skin and ulcers), psychological (e.g., depression), and vascular (e.g., Raynaud's, ulcers).

Additional symptoms of systemic sclerosis can include, for example, swelling, then thickening and tightening of the skin at the ends of the fingers. Raynaud phenomenon, in which the fingers suddenly and temporarily become very pale and tingle or become numb, painful, or both in response to cold or emotional upset (see Raynaud Syndrome), is also common. Fingers may become bluish or white. Heartburn, difficulty in swallowing, and shortness of breath are occasionally the first symptoms of systemic sclerosis. Aches and pains in several joints often accompany early symptoms. Sometimes inflammation of the muscles (polymyositis), with its accompanying muscle pain and weakness, develops.

Other symptoms include changes in the skin, joint, gastrointestinal system, lung, heart and kidney.

The skin can become more widely taut, shiny, and darker than usual. Sometimes dilated blood vessels (telangiectasia often referred to as spider veins) can appear on the fingers, chest, face, lips, and tongue, and bumps composed of calcium can develop on the fingers, on other bony areas, or at the joints. Sores can develop on the fingertips and knuckles.

In the joints, sometimes, a grating sound can be felt or heard as inflamed tissues move over each other, particularly at and below the knees and at the elbows and wrists. The fingers, wrists, and elbows may become stuck in flexed positions because of scarring in the skin.

In the GI system, scarring can damage the lower end of the esophagus and swallowing difficulties and heartburn can develop. Abnormal cell growth in the esophagus can occurs and increases one's risk of esophageal blockage due to a fibrous band or one's risk of esophageal cancer. Damage to the intestines can interfere with food absorption and cause weight loss.

Systemic sclerosis can cause scar tissue to accumulate in the lungs, resulting in abnormal shortness of breath during exercise. The blood vessels that supply the lungs can be affected (their walls thicken), so they cannot carry as much blood. Therefore, blood pressure within the arteries that supply the lungs can increase (PAH). Systemic sclerosis can also cause several life-threatening heart abnormalities, including heart failure and abnormal rhythms.

Severe kidney disease can result from systemic sclerosis. The first symptom of kidney damage may be an abrupt, progressive rise in blood pressure.

Symptoms of PAH

Symptoms of PAH include but are not limited to shortness of breath, chest pain, fatigue, fainting, and swelling in ankles and legs.

Anti-Vinculin Antibodies

In various embodiments, the anti-vinculin antibody detected in these methods or systems is an antibody that binds specifically to vinculin or a fragment thereof.

In various embodiments, the anti-vinculin antibody is an antibody that binds specifically to a 5, 6, 7, 8, 9, 10, 11, 12, 13, 14, 15, 16, 17, 18, 19, 20, 21, or 22 residue polypeptide that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of vinculin.

In another embodiment, the anti-vinculin antibody binds specifically to a polypeptide comprising 5, 6, 7, 8, 9, 10, 11, 12, 13, 14, 15, 16, 17, 18, 19, 20, 21, or 22 residues that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of vinculin.

In another embodiment, the anti-vinculin antibody binds specifically to a polypeptide comprising or consisting of 5, 6, 7, 8, 9, 10, 11, 12, 13, 14, 15, 16, 17, 18, 19, 20, 21, or 22 contiguous residues of vinculin.

In various embodiments, the anti-vinculin antibody is an antibody that binds specifically to a polypeptide having SEQ ID NO:1.

In various embodiments, the anti-vinculin antibody is an antibody that binds specifically to a 5, 6, 7, 8, 9, 10, 11, 12, 13, 14, 15, 16, 17, 18, 19, 20, 21, or 22 residue polypeptide that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of SEQ ID NO:1.

In another embodiment, the anti-vinculin antibody binds specifically to a polypeptide comprising 5, 6, 7, 8, 9, 10, 11, 12, 13, 14, 15, 16, 17, 18, 19, 20, 21, or 22 residues that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of SEQ ID NO:1.

In another embodiment, the anti-vinculin antibody binds specifically to a polypeptide comprising or consisting of 5, 6, 7, 8, 9, 10, 11, 12, 13, 14, 15, 16, 17, 18, 19, 20, 21, or 22 contiguous residues of SEQ ID NO:1.

Contiguous residues of vinculin or SEQ ID NO:1 include those beginning at any amino acid and ending at any amino acid of vinculin or SEQ ID NO:1.

These polypeptides as described above can also be used as fragments of vinculin in the assay to determine the presence and the level of anti-vinculin antibodies.

```
Protein sequence of Vinculin (SEQ ID NO: 1):
MPVFHTRTIESILEPVAQQISHLVIMHEEGEVDGKAIPDLTAPVAAVQA

AVSNLVRVGKETVQTTEDQILKRDMPPAFIKVENACTKLVQAAQMLQSD

PYSVPARDYLIDGSRGILSGTSDLLLTFDEAEVRKIIRVCKGILEYLTV

AEVVETMEDLVTYTKNLGPGMTKMAKMIDERQQELTHQEHRVMLVNSMN

TVKELLPVLISAMKIFVTTKNSKNQGIEEALKNRNFTVEKMSAEINEII

RVLQLTSWDEDAWASKDTEAMKRALASIDSKLNQAKGWLRDPSASPGDA

GEQAIRQILDEAGKVGELCAGKERREILGTCKMLGQMTDQVADLRARGQ

GSSPVAMQKAQQVSQGLDVLTAKVENAARKLEAMTNSKQSIAKKIDAAQ

NWLADPNGGPEGEEQIRGALAEARKIAELCDDPKERDDILRSLGEISAL

TSKLADLRRQGKGDSPEARALAKQVATALQNLQTKTNRAVANSRPAKAA

VHLEGKIEQAQRWIDNPTVDDRGVGQAAIRGLVAEGHRLANVMMGPYRQ

DLLAKCDRVDQLTAQLADLAARGEGESPQARALASQLQDSLKDLKARMQ

EAMTQEVSDVFSDTTTPIKLLAVAATAPPDAPNREEVEDERAANFENHS

GKLGATAEKAAAVGTANKSTVEGIQASVKTARELTPQVVSAARILLRNP

GNQAAYEHFETMKNQWIDNVEKMTGLVDEAIDTKSLLDASEEAIKKDLD

KCKVAMANIQPQMLVAGATSIARRANRILLVAKREVENSEDPKFREAVK

AASDELSKTISPMVMDAKAVAGNISDPGLQKSFLDSGYRILGAVAKVRE

AFQPQEPDFPPPPPDLEQLRLTDELAPPKPPLPEGEVPPPRPPPPEEKD
```

-continued

```
EEFPEQKAGEVINQPMMMAARQLHDEARKWSSKGNDIIAAAKRMALLMA

EMSRLVRGGSGTKRALIQCAKDIAKASDEVTRLAKEVAKQCTDKRIRTN

LLQVCERIPTISTQLKILSTVKATMLGRTNISDEESEQATEMLVHNAQN

LMQSVKETVREAEAASIKIRTDAGFTLRWVRKTPWYQ
```

Biological Samples

Examples of biological samples include but are not limited to body fluids, whole blood, serum, plasma, pulmonary secretions, intestinal fluids or aspirate, stomach fluids or aspirate, cerebral spinal fluid (CSF), urine, sweat, saliva, tears, breast aspirate, prostate fluid, seminal fluid, cervical scraping, amniotic fluid, intraocular fluid, mucous, and stool. In particular embodiments of the present invention, the biological sample is whole blood, blood plasma, blood serum, or pulmonary secretions. In various embodiments, the biological sample is whole blood. In various embodiments, the biological sample is serum. In various embodiments, the biological sample is plasma.

Reference Value

In some embodiments, the reference value can be established from biological samples from healthy subjects.

For example, if the biological sample is serum, then the reference value can be obtained from serum samples of healthy subjects (e.g., subjects who do not have systemic sclerosis and/or irritable bowel syndrome). In other embodiments, the reference value is the average anti-vinculin antibody level for the same type of biological sample from a population of healthy subjects. In other embodiments, the reference value is the average plus one or two standard deviations of average anti-vinculin antibody level for the same type of biological sample from a population of healthy subjects. In some embodiments, the population of healthy subjects can range from at least three healthy individuals to 25 healthy individuals, and even more than 50 healthy individuals (e.g., 50-75, 75-100, 100-200, 200-300, 300-400, 400-500).

In some embodiments, optical density is used as a measurement of antibody levels.

In certain embodiments, optical density (OD) is used to measure the level of anti-vinculin antibodies. In certain embodiments, when the OD of anti-vinculin antibodies (ODv) is greater than 1.62, 1.86 or 2.23 the subject is determined to have systemic sclerosis. In various embodiments, when the OD of anti-vinculin antibodies (ODv) is greater than 1.00, 1.25, 1.50, 1.75, 2.00, 2.25, 2.50 2.75 the subject is determined to have systemic sclerosis. In certain embodiments, these OD numbers are based on a dilution of the biological sample of 1:32 and antigen concentration of 1.2 ug/ml.

In other embodiments, the ODv cutoff points can be determined based on different dilutions of the biological sample and the antigens and are included within the embodiments of the present invention.

Treatments

In further embodiments, the above determinations may be used to select the treatment for the subject. In one embodiment, a subject with the likely presence of systemic sclerosis may be treated with one or more therapies for systemic sclerosis. One of ordinary skill in the art will be able to select an available treatment for systemic sclerosis based on the diagnosis of systemic sclerosis.

In various embodiments, the available therapy comprises administering a course of antibiotic therapy to treat the systemic sclerosis. Examples of antibiotics include but are not limited to aminoglycosides (e.g., amikacin, gentamicin, kanamycin, neomycin, netilmicin, streptomycin, tobramycin, paromomycin), ansamycins (e.g., geldanamycin, herbimycin), carbacephems (e.g., loracarbef), carbapenems (e.g., ertapenem, doripenem, imipenem, cilastatin, meropenem), cephalosporins (e.g., first generation: cefadroxil, cefazolin, cefalotin or cefalothin, cefalexin; second generation: cefaclor, cefamandole, cefoxitin, cefprozil, cefuroxime; third generation: cefixime, cefdinir, cefditoren, cefoperazone, cefotaxime, cefpodoxime, ceftazidime, ceftibuten, ceftizoxime, ceftriaxone; fourth generation: cefepime; fifth generation: ceftobiprole), glycopeptides (e.g., teicoplanin, vancomycin), macrolides (e.g., azithromycin, clarithromycin, dirithromycin, erythromycin, roxithromycin, troleandomycin, telithromycin, spectinomycin), monobactams (e.g., aztreonam), penicillins (e.g., amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin), antibiotic polypeptides (e.g., bacitracin, colistin, polymyxin b), quinolones (e.g., ciprofloxacin, enoxacin, gatifloxacin, levofloxacin, lomefloxacin, moxifloxacin, norfloxacin, ofloxacin, trovafloxacin), rifamycins (e.g., rifampicin or rifampin, rifabutin, rifapentine, rifaximin), sulfonamides (e.g., mafenide, prontosil, sulfacetamide, sulfamethizole, sulfanilamide, sulfasalazine, sulfisoxazole, trimethoprim, trimethoprim-sulfamethoxazole (co-trimoxazole, "tmp-smx"), and tetracyclines (e.g., demeclocycline, doxycycline, minocycline, oxytetracycline, tetracycline) as well as arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin combination, and tinidazole, or a combination thereof. In various embodiments, the antibiotics are a combination of rifaximin and neomycin. In various embodiments, the antibiotics are a combination of rifaximin and doxycycline. In various embodiments, the antibiotics are a combination of rifaximin and metronidazole.

In various embodiments, the antibiotics are non-absorbable antibiotics. Examples of non-absorbable antibiotics include but are not limited to rifaximin, neomycin, Bacitracin, vancomycin, teicoplanin, ramoplanin, and paramomycin.

In various embodiments, the therapy is an available therapy in the prior art.

Examples of therapies, include but are not limited to, treatments directed at symptom relief, such as (but not limited to) NSAIDS, antacids (including proton pump inhibitors and H2 blockers), vasoactive drugs (e.g., nifedipine, sidenafil), immunosuppressives (e.g., methotrexate, tacrolimus, mycopenolate, cyclophosphamide, biologics such rituximab, tocilizumab) and stem cell transplantation.

In various embodiments, the method can comprise providing an anti-vinculin antibody neutralizing or inhibiting agent and administering the anti-vinculin antibody neutralizing or inhibiting agent to a subject in need thereof to neutralize or inhibit the anti-vinculin antibody.

In various embodiments, the anti-vinculin antibody neutralizing or inhibiting agent is a polypeptide capable of binding to the anti-vinculin antibody and neutralizing or inhibiting its function.

In various embodiments, the anti-vinculin antibody neutralizing or inhibiting agent is a polypeptide capable of binding to an antigen binding site of the anti-vinculin antibody. While not wishing to be bound by any particular theory, the inventors believe that these polypeptides can serves as a decoy to the anti-vinculin antibody. In various embodiments, the polypeptides are CDT pentapeptides as disclosed by Lucchese and Delfino (*Developing an anti-Campylobacter jejuni vaccine*. Immunopharmacology and Immunotoxicology, 2012; Early Online: 1-6), which is hereby incorporated by reference in its entirety as though fully set forth.

In various embodiments, the anti-vinculin antibody neutralizing or inhibiting agent is a small molecule capable of binding to the anti-vinculin antibody and neutralizing or inhibiting its function.

In various embodiments, the anti-vinculin antibody neutralizing or inhibiting agent is a small molecule capable of binding to an antigen binding site of the anti-vinculin antibody.

In various embodiments, the method can comprise providing an agent to change vinculin from an inactive state to an active state; and administering the agent to a subject in need thereof to treat systemic sclerosis.

In various embodiments, the agent to change vinculin from an inactive state to an active state is a small molecule capable of activating vinculin.

In various embodiments, the method can comprise providing a vinculin agonist; and administering the vinculin agonist to a subject in need thereof to treat systemic sclerosis. In certain embodiments, the vinculin agonist can be vinculin activating peptide (VAP) as disclosed by Nelson et al., *Vinculin Activators Target Integrins from Within the Cell to Increase Melanoma Sensitivity to Chemotherapy*, MOL CANCER RES JUNE 2011 9; 712 (published online Apr. 1, 2011), which is hereby incorporated by reference in its entirety as though fully set forth. In various embodiments, the VAP can be residues 500-633 of invasin protein IpaA of *Shigella*.

The protein sequence of IpaA of *Shigella*:

```
                                         (SEQ ID NO: 2)
MHNVNNTQAP TFLYKATSPS STEYSELKSK ISDIHSSQTS

LKTPASVSEK ENFATSFNQK CLDFLFSSSG KEDVLRSIYS

NSMNAYAKSE ILEFSNVLYS LVHQNGLNFE NEKGLQKIVA

QYSELIIKDK LSQDSAFGPW SAKNKKLHQL RQNIEHRLAL

LAQQHTSGEA LSLGQKLLNT EVSSFIKNNI LAELKLSNET

VSSLKLDDLV DAQAKLAFDS LRNQRKNTID SKGFGIGKLS

RDLNTVAVFP ELLRKVLNDI LEDIKDSHPI QDGLPTPPED

MPDGGPTPGA NEKTSQPVIH YHINNDNRTY DNRVFDNRVY

DNSYHENPEN DAQSPTSQTN DLLSRNGNSL LNPQRALVQK

VTSVLPHSIS DTVQTFANNS ALEKVFNHTP DNSDGIGSDL

LTTSSQERSA NNSLSRGHRP LNIQNSSTTP PLHPEGVTSS

NDNSSDTTKS SASLSHRVAS QINKFNSNTD SKVLQTDFLS

RNGDTYLTRE TIFEASKKVT NSLSNLISLI GTKSGTQERE

LQEKSKDITK STTEHRINNK LKVTDANIRN YVTETNADTI

DKNHAIYEKA KEVSSALSKV LSKIDDTSAE LLTDDISDLK

NNNDITAENN NIYKAAKDVT TSLSKVLKNI NKD
```

In various embodiments, the method can comprise providing a vinculin activator; and administering the vinculin activator to a subject in need thereof to treat systemic sclerosis. In certain embodiments, the vinculin activator can be talin, f-actin, a-catenin, or combinations thereof.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Serum samples from 72 SSc patients meeting the ACR/EULAR 2013 criteria were recruited. Serum levels of anti-CdtB and anti-vinculin antibodies were determined by ELISA. Clinical assessments, procedures, questionnaires and lab results were obtained from medical charts for clinical correlations.

From a total of 72 SSc patients available for analysis, 32 Patients had diffuse SSc subtype (48.4%), mean age was 56.4, 18 patients (25%) were positive for lactulose breath testing, mean GIT 2.0 is (0.373). ILD is present in 40 (55%) and PAH present 23(31%). Table. 1

TABLE 1

| Demographics | |
|---|---|
| Variable | (N) Mean ± SD or Freq |
| Age | (72) 56.4 ± 13.8 |
| Body Mass Index (BMI) | (71) 24.3 ± 4.3 |
| Diabetic | (3) 4.17% |
| Hypertension | (23) 31.94% |
| Subtype Diffuse | (32) 48.48% |
| Pulmonary Artery Hypertension (PAH) | (23) 31.94% |
| Interstitial lung disease (ILD) | (40) 55.56% |
| Ulcer | (17) 25.76% |
| Positive breath test | (18) 66.67% |
| Gastrointestinal Tract (GIT) | (46) 0.373 ± 0.312 |
| Skin score | (62) 6.40 ± 6.75 |
| Health Assessment Questionnaire (HAQ) | (47) 0.997 ± 1.471 |
| Forced Vital Capacity (FVC) | (65) 79.8 ± 26.1 |
| low carbon monoxide diffusion capacity hemoglobin (DLCO Hgb) | (58) 57.0 ± 26.9 |
| Complete blood count hemoglobin (CBC Hgb) | (59) 12.3 ± 1.8 |
| Creatinine | (57) 0.936 ± 0.660 |

Using the cut-off points used for IBS, 29 (40%) out of 72 pts were positive for vinculin. Only one patient was positive for anti-CdtB. Linear regression analysis for anti-vinculin identified BMI (p value<0.005) and PAH (p value<0.052) as significant predictors of higher anti-vinculin in SSc patients. In contrast, GI measures such as GIT 2.0 (p value<0.920) and lactulose breath testing (p value <0.157) did not show in significance. Further regression analysis for predictors of PAH with higher vinculin levels revealed smoking (current or former) as a significant (p value <0.01) predictor FIG. 1.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

What is claimed is:

1. A method of measuring the level of anti-vinculin antibodies in a subject who has systemic sclerosis, comprising:
    measuring a level of anti-vinculin antibodies in a whole blood, serum or plasma sample obtained from the subject who has systemic sclerosis by using vinculin or a fragment thereof to assay the biological sample.

2. The method of claim 1, wherein the vinculin or a fragment thereof is SEQ ID NO: 1 or a fragment thereof.

3. The method of claim 1, wherein measuring the level of anti-vinculin antibodies comprises using enzyme-linked immunosorbent assay (ELISA).

4. The method of claim 1, wherein measuring the level of anti-vinculin antibodies comprises using immunohistochemistry, flow cytometry, fluorescence in situ hybridization (FISH), radioimmuno assay, or affinity purification.

5. A method of selecting a therapy for systemic sclerosis for a subject who has systemic sclerosis, comprising:
    measuring a level of anti-vinculin antibodies by the method of claim 1; and
    selecting a therapy for systemic sclerosis to treat systemic sclerosis when the level of anti-vinculin antibodies is higher than a reference value.

6. The method of claim 1, wherein measuring the level of anti-vinculin antibodies in a biological sample comprises using vinculin protein or the fragment thereof at about 1.2 µg/ml concentration.

7. The method of claim 1, wherein measuring the level of anti-vinculin antibodies in a biological sample comprises using the biological sample used at about 1:32 dilution.

8. The method of claim 5, wherein the selected therapy is a course of antibiotic therapy.

* * * * *

SEQUENCE LISTING

```
<160> NUMBER OF SEQ ID NOS: 2

<210> SEQ ID NO 1
<211> LENGTH: 1066
<212> TYPE: PRT
<213> ORGANISM: Homo sapiens

<400> SEQUENCE: 1

Met Pro Val Phe His Thr Arg Thr Ile Glu Ser Ile Leu Glu Pro Val
1               5                   10                  15

Ala Gln Gln Ile Ser His Leu Val Ile Met His Glu Glu Gly Glu Val
            20                  25                  30

Asp Gly Lys Ala Ile Pro Asp Leu Thr Ala Pro Val Ala Ala Val Gln
        35                  40                  45

Ala Ala Val Ser Asn Leu Val Arg Val Gly Lys Glu Thr Val Gln Thr
    50                  55                  60

Thr Glu Asp Gln Ile Leu Lys Arg Asp Met Pro Pro Ala Phe Ile Lys
65                  70                  75                  80

Val Glu Asn Ala Cys Thr Lys Leu Val Gln Ala Ala Gln Met Leu Gln
                85                  90                  95

Ser Asp Pro Tyr Ser Val Pro Ala Arg Asp Tyr Leu Ile Asp Gly Ser
            100                 105                 110

Arg Gly Ile Leu Ser Gly Thr Ser Asp Leu Leu Leu Thr Phe Asp Glu
        115                 120                 125

Ala Glu Val Arg Lys Ile Ile Arg Val Cys Lys Gly Ile Leu Glu Tyr
    130                 135                 140

Leu Thr Val Ala Glu Val Val Glu Thr Met Glu Asp Leu Val Thr Tyr
145                 150                 155                 160
```

-continued

Thr Lys Asn Leu Gly Pro Gly Met Thr Lys Met Ala Lys Met Ile Asp
            165                 170                 175
Glu Arg Gln Gln Glu Leu Thr His Gln Glu His Arg Val Met Leu Val
            180                 185                 190
Asn Ser Met Asn Thr Val Lys Glu Leu Leu Pro Val Leu Ile Ser Ala
            195                 200                 205
Met Lys Ile Phe Val Thr Thr Lys Asn Ser Lys Asn Gln Gly Ile Glu
    210                 215                 220
Glu Ala Leu Lys Asn Arg Asn Phe Thr Val Glu Lys Met Ser Ala Glu
225                 230                 235                 240
Ile Asn Glu Ile Ile Arg Val Leu Gln Leu Thr Ser Trp Asp Glu Asp
            245                 250                 255
Ala Trp Ala Ser Lys Asp Thr Glu Ala Met Lys Arg Ala Leu Ala Ser
            260                 265                 270
Ile Asp Ser Lys Leu Asn Gln Ala Lys Gly Trp Leu Arg Asp Pro Ser
            275                 280                 285
Ala Ser Pro Gly Asp Ala Gly Glu Gln Ala Ile Arg Gln Ile Leu Asp
            290                 295                 300
Glu Ala Gly Lys Val Gly Glu Leu Cys Ala Gly Lys Glu Arg Arg Glu
305                 310                 315                 320
Ile Leu Gly Thr Cys Lys Met Leu Gly Gln Met Thr Asp Gln Val Ala
            325                 330                 335
Asp Leu Arg Ala Arg Gly Gln Gly Ser Ser Pro Val Ala Met Gln Lys
            340                 345                 350
Ala Gln Gln Val Ser Gln Gly Leu Asp Val Leu Thr Ala Lys Val Glu
            355                 360                 365
Asn Ala Ala Arg Lys Leu Glu Ala Met Thr Asn Ser Lys Gln Ser Ile
            370                 375                 380
Ala Lys Lys Ile Asp Ala Ala Gln Asn Trp Leu Ala Asp Pro Asn Gly
385                 390                 395                 400
Gly Pro Glu Gly Glu Glu Gln Ile Arg Gly Ala Leu Ala Glu Ala Arg
            405                 410                 415
Lys Ile Ala Glu Leu Cys Asp Asp Pro Lys Glu Arg Asp Asp Ile Leu
            420                 425                 430
Arg Ser Leu Gly Glu Ile Ser Ala Leu Thr Ser Lys Leu Ala Asp Leu
            435                 440                 445
Arg Arg Gln Gly Lys Gly Asp Ser Pro Glu Ala Arg Ala Leu Ala Lys
            450                 455                 460
Gln Val Ala Thr Ala Leu Gln Asn Leu Gln Thr Lys Thr Asn Arg Ala
465                 470                 475                 480
Val Ala Asn Ser Arg Pro Ala Lys Ala Ala Val His Leu Glu Gly Lys
            485                 490                 495
Ile Glu Gln Ala Gln Arg Trp Ile Asp Asn Pro Thr Val Asp Asp Arg
            500                 505                 510
Gly Val Gly Gln Ala Ala Ile Arg Gly Leu Val Ala Glu Gly His Arg
            515                 520                 525
Leu Ala Asn Val Met Met Gly Pro Tyr Arg Gln Asp Leu Leu Ala Lys
            530                 535                 540
Cys Asp Arg Val Asp Gln Leu Thr Ala Gln Leu Ala Asp Leu Ala Ala
545                 550                 555                 560
Arg Gly Glu Gly Glu Ser Pro Gln Ala Arg Ala Leu Ala Ser Gln Leu
            565                 570                 575

```
Gln Asp Ser Leu Lys Asp Leu Lys Ala Arg Met Gln Glu Ala Met Thr
            580                 585                 590

Gln Glu Val Ser Asp Val Phe Ser Asp Thr Thr Thr Pro Ile Lys Leu
        595                 600                 605

Leu Ala Val Ala Ala Thr Ala Pro Pro Asp Ala Pro Asn Arg Glu Glu
    610                 615                 620

Val Phe Asp Glu Arg Ala Ala Asn Phe Glu Asn His Ser Gly Lys Leu
625                 630                 635                 640

Gly Ala Thr Ala Glu Lys Ala Ala Val Gly Thr Ala Asn Lys Ser
            645                 650                 655

Thr Val Glu Gly Ile Gln Ala Ser Val Lys Thr Ala Arg Glu Leu Thr
            660                 665                 670

Pro Gln Val Val Ser Ala Ala Arg Ile Leu Leu Arg Asn Pro Gly Asn
        675                 680                 685

Gln Ala Ala Tyr Glu His Phe Glu Thr Met Lys Asn Gln Trp Ile Asp
        690                 695                 700

Asn Val Glu Lys Met Thr Gly Leu Val Asp Glu Ala Ile Asp Thr Lys
705                 710                 715                 720

Ser Leu Leu Asp Ala Ser Glu Glu Ala Ile Lys Lys Asp Leu Asp Lys
            725                 730                 735

Cys Lys Val Ala Met Ala Asn Ile Gln Pro Gln Met Leu Val Ala Gly
            740                 745                 750

Ala Thr Ser Ile Ala Arg Arg Ala Asn Arg Ile Leu Leu Val Ala Lys
            755                 760                 765

Arg Glu Val Glu Asn Ser Glu Asp Pro Lys Phe Arg Glu Ala Val Lys
        770                 775                 780

Ala Ala Ser Asp Glu Leu Ser Lys Thr Ile Ser Pro Met Val Met Asp
785                 790                 795                 800

Ala Lys Ala Val Ala Gly Asn Ile Ser Asp Pro Gly Leu Gln Lys Ser
            805                 810                 815

Phe Leu Asp Ser Gly Tyr Arg Ile Leu Gly Ala Val Ala Lys Val Arg
            820                 825                 830

Glu Ala Phe Gln Pro Gln Glu Pro Asp Phe Pro Pro Pro Pro Pro Asp
        835                 840                 845

Leu Glu Gln Leu Arg Leu Thr Asp Glu Leu Ala Pro Pro Lys Pro Pro
    850                 855                 860

Leu Pro Glu Gly Glu Val Pro Pro Pro Arg Pro Pro Pro Pro Glu Glu
865                 870                 875                 880

Lys Asp Glu Glu Phe Pro Glu Gln Lys Ala Gly Glu Val Ile Asn Gln
            885                 890                 895

Pro Met Met Met Ala Ala Arg Gln Leu His Asp Glu Ala Arg Lys Trp
        900                 905                 910

Ser Ser Lys Gly Asn Asp Ile Ile Ala Ala Lys Arg Met Ala Leu
        915                 920                 925

Leu Met Ala Glu Met Ser Arg Leu Val Arg Gly Gly Ser Gly Thr Lys
    930                 935                 940

Arg Ala Leu Ile Gln Cys Ala Lys Asp Ile Ala Lys Ala Ser Asp Glu
945                 950                 955                 960

Val Thr Arg Leu Ala Lys Glu Val Ala Lys Gln Cys Thr Asp Lys Arg
            965                 970                 975

Ile Arg Thr Asn Leu Leu Gln Val Cys Glu Arg Ile Pro Thr Ile Ser
            980                 985                 990

Thr Gln Leu Lys Ile Leu Ser Thr  Val Lys Ala Thr Met  Leu Gly Arg
```

```
            995                 1000                1005
Thr  Asn  Ile  Ser  Asp  Glu  Glu  Ser  Glu  Gln  Ala  Thr  Glu  Met  Leu
         1010                 1015                1020

Val  His  Asn  Ala  Gln  Asn  Leu  Met  Gln  Ser  Val  Lys  Glu  Thr  Val
         1025                 1030                1035

Arg  Glu  Ala  Glu  Ala  Ala  Ser  Ile  Lys  Ile  Arg  Thr  Asp  Ala  Gly
         1040                 1045                1050

Phe  Thr  Leu  Arg  Trp  Val  Arg  Lys  Thr  Pro  Trp  Tyr  Gln
         1055                 1060                1065

<210> SEQ ID NO 2
<211> LENGTH: 633
<212> TYPE: PRT
<213> ORGANISM: Shigella

<400> SEQUENCE: 2

Met  His  Asn  Val  Asn  Asn  Thr  Gln  Ala  Pro  Thr  Phe  Leu  Tyr  Lys  Ala
1                  5                   10                  15

Thr  Ser  Pro  Ser  Ser  Thr  Glu  Tyr  Ser  Glu  Leu  Lys  Ser  Lys  Ile  Ser
                  20                   25                  30

Asp  Ile  His  Ser  Ser  Gln  Thr  Ser  Leu  Lys  Thr  Pro  Ala  Ser  Val  Ser
             35                   40                  45

Glu  Lys  Glu  Asn  Phe  Ala  Thr  Ser  Phe  Asn  Gln  Lys  Cys  Leu  Asp  Phe
        50                  55                  60

Leu  Phe  Ser  Ser  Ser  Gly  Lys  Glu  Asp  Val  Leu  Arg  Ser  Ile  Tyr  Ser
65                  70                  75                  80

Asn  Ser  Met  Asn  Ala  Tyr  Ala  Lys  Ser  Glu  Ile  Leu  Glu  Phe  Ser  Asn
                  85                  90                  95

Val  Leu  Tyr  Ser  Leu  Val  His  Gln  Asn  Gly  Leu  Asn  Phe  Glu  Asn  Glu
             100                 105                 110

Lys  Gly  Leu  Gln  Lys  Ile  Val  Ala  Gln  Tyr  Ser  Glu  Leu  Ile  Ile  Lys
        115                 120                 125

Asp  Lys  Leu  Ser  Gln  Asp  Ser  Ala  Phe  Gly  Pro  Trp  Ser  Ala  Lys  Asn
    130                 135                 140

Lys  Lys  Leu  His  Gln  Leu  Arg  Gln  Asn  Ile  Glu  His  Arg  Leu  Ala  Leu
145                 150                 155                 160

Leu  Ala  Gln  Gln  His  Thr  Ser  Gly  Glu  Ala  Leu  Ser  Leu  Gly  Gln  Lys
                 165                 170                 175

Leu  Leu  Asn  Thr  Glu  Val  Ser  Ser  Phe  Ile  Lys  Asn  Asn  Ile  Leu  Ala
             180                 185                 190

Glu  Leu  Lys  Leu  Ser  Asn  Glu  Thr  Val  Ser  Ser  Leu  Lys  Leu  Asp  Asp
        195                 200                 205

Leu  Val  Asp  Ala  Gln  Ala  Lys  Leu  Ala  Phe  Asp  Ser  Leu  Arg  Asn  Gln
    210                 215                 220

Arg  Lys  Asn  Thr  Ile  Asp  Ser  Lys  Gly  Phe  Gly  Ile  Gly  Lys  Leu  Ser
225                 230                 235                 240

Arg  Asp  Leu  Asn  Thr  Val  Ala  Val  Phe  Pro  Glu  Leu  Leu  Arg  Lys  Val
                 245                 250                 255

Leu  Asn  Asp  Ile  Leu  Glu  Asp  Ile  Lys  Asp  Ser  His  Pro  Ile  Gln  Asp
             260                 265                 270

Gly  Leu  Pro  Thr  Pro  Pro  Glu  Asp  Met  Pro  Asp  Gly  Gly  Pro  Thr  Pro
        275                 280                 285

Gly  Ala  Asn  Glu  Lys  Thr  Ser  Gln  Pro  Val  Ile  His  Tyr  His  Ile  Asn
    290                 295                 300
```

-continued

```
Asn Asp Asn Arg Thr Tyr Asp Asn Arg Val Phe Asp Asn Arg Val Tyr
305                 310                 315                 320

Asp Asn Ser Tyr His Glu Asn Pro Glu Asn Asp Ala Gln Ser Pro Thr
                325                 330                 335

Ser Gln Thr Asn Asp Leu Leu Ser Arg Asn Gly Asn Ser Leu Leu Asn
                340                 345                 350

Pro Gln Arg Ala Leu Val Gln Lys Val Thr Ser Val Leu Pro His Ser
            355                 360                 365

Ile Ser Asp Thr Val Gln Thr Phe Ala Asn Asn Ser Ala Leu Glu Lys
        370                 375                 380

Val Phe Asn His Thr Pro Asp Asn Ser Asp Gly Ile Gly Ser Asp Leu
385                 390                 395                 400

Leu Thr Thr Ser Ser Gln Glu Arg Ser Ala Asn Asn Ser Leu Ser Arg
                405                 410                 415

Gly His Arg Pro Leu Asn Ile Gln Asn Ser Ser Thr Thr Pro Pro Leu
                420                 425                 430

His Pro Glu Gly Val Thr Ser Ser Asn Asp Asn Ser Ser Asp Thr Thr
            435                 440                 445

Lys Ser Ser Ala Ser Leu Ser His Arg Val Ala Ser Gln Ile Asn Lys
450                 455                 460

Phe Asn Ser Asn Thr Asp Ser Lys Val Leu Gln Thr Asp Phe Leu Ser
465                 470                 475                 480

Arg Asn Gly Asp Thr Tyr Leu Thr Arg Glu Thr Ile Phe Glu Ala Ser
                485                 490                 495

Lys Lys Val Thr Asn Ser Leu Ser Asn Leu Ile Ser Leu Ile Gly Thr
            500                 505                 510

Lys Ser Gly Thr Gln Glu Arg Glu Leu Gln Glu Lys Ser Lys Asp Ile
            515                 520                 525

Thr Lys Ser Thr Thr Glu His Arg Ile Asn Asn Lys Leu Lys Val Thr
530                 535                 540

Asp Ala Asn Ile Arg Asn Tyr Val Thr Glu Thr Asn Ala Asp Thr Ile
545                 550                 555                 560

Asp Lys Asn His Ala Ile Tyr Glu Lys Ala Lys Glu Val Ser Ser Ala
                565                 570                 575

Leu Ser Lys Val Leu Ser Lys Ile Asp Asp Thr Ser Ala Glu Leu Leu
            580                 585                 590

Thr Asp Asp Ile Ser Asp Leu Lys Asn Asn Asn Asp Ile Thr Ala Glu
            595                 600                 605

Asn Asn Asn Ile Tyr Lys Ala Ala Lys Asp Val Thr Thr Ser Leu Ser
            610                 615                 620

Lys Val Leu Lys Asn Ile Asn Lys Asp
625                 630
```